(12) United States Patent
Tal et al.

(10) Patent No.: US 11,471,646 B2
(45) Date of Patent: Oct. 18, 2022

(54) MICROCATHETER

(71) Applicant: ACCURATE MEDICAL THERAPEUTICS LTD., Tel-Aviv (IL)

(72) Inventors: Michael Gabriel Tal, Savyon (IL); Eran Miller, Moshav Beit Elazari (IL)

(73) Assignee: ACCURATE MEDICAL THERAPEUTICS LTD, Tel-Aviv (IL)

( * ) Notice: Subject to any disclaimer, the term of this patent is extended or adjusted under 35 U.S.C. 154(b) by 367 days.

(21) Appl. No.: 16/634,344

(22) PCT Filed: Aug. 8, 2018

(86) PCT No.: PCT/IL2018/050882
§ 371 (c)(1),
(2) Date: Jan. 27, 2020

(87) PCT Pub. No.: WO2019/030761
PCT Pub. Date: Feb. 14, 2019

(65) Prior Publication Data
US 2020/0230355 A1     Jul. 23, 2020

Related U.S. Application Data

(60) Provisional application No. 62/542,960, filed on Aug. 9, 2017.

(51) Int. Cl.
*A61M 25/00* (2006.01)
*A61L 29/04* (2006.01)
(Continued)

(52) U.S. Cl.
CPC ....... *A61M 25/0053* (2013.01); *A61L 29/049* (2013.01); *A61M 25/0009* (2013.01);
(Continued)

(58) Field of Classification Search
CPC .......... A61M 25/0053; A61M 25/0012; A61M 25/0108; A61M 2025/0042;
(Continued)

(56) References Cited

U.S. PATENT DOCUMENTS 5,730,733 A * 3/1998 Mortier ............... A61M 25/005
604/527
2002/0156459 A1* 10/2002 Ye ..................... A61M 25/0053
604/527
(Continued)

FOREIGN PATENT DOCUMENTS

CN          1639495       7/2005
CN          101001658     7/2007
(Continued)

OTHER PUBLICATIONS

International Search Report for International Application No. PCT/IL2018/050882 dated Oct. 29, 2018.
(Continued)

*Primary Examiner* — Amber R Stiles
(74) *Attorney, Agent, or Firm* — The Roy Gross Law Firm, LLC; Roy Gross

(57) ABSTRACT

A microcatheter comprising an inner layer, a strike layer and an outer layer and a braided skeleton located between the inner layer and the outer layer, wherein the inner layer is made of Polytetrafluoroethylene (PTFE) and has a thickness of 0.0015 inch or less, wherein the strike layer includes a polyether block amide and has a thickness of 0.001 inch or less, and wherein a distal portion of said outer layer is made of polycarbonate-based thermoplastic polyurethane having a shore of 90A or below.

14 Claims, 1 Drawing Sheet

(51) Int. Cl.
*A61M 25/01* (2006.01)
*B29C 61/02* (2006.01)
*B29C 63/00* (2006.01)
*B29C 63/18* (2006.01)
*B29K 675/00* (2006.01)
*B29L 31/00* (2006.01)

(52) U.S. Cl.
CPC .... *A61M 25/0012* (2013.01); *A61M 25/0108* (2013.01); *B29C 61/025* (2013.01); *B29C 63/0017* (2013.01); *B29C 63/0069* (2013.01); *B29C 63/18* (2013.01); *A61M 2025/0042* (2013.01); *B29K 2675/00* (2013.01); *B29L 2031/7542* (2013.01)

(58) Field of Classification Search
CPC ........... A61M 25/0045; A61M 25/0009; A61L 29/049; A61L 29/041; A61L 29/02; A61L 29/126; A61L 29/18; B29C 61/025; B29C 63/0017; B29C 63/0069; B29C 63/18; B29K 2675/00; B29L 2031/7542; C08L 27/18; C08L 75/04; C08L 77/00
See application file for complete search history.

(56) References Cited

U.S. PATENT DOCUMENTS

| | | | |
|---|---|---|---|
| 2002/0198492 A1* | 12/2002 | Miller | A61M 25/1027 604/96.01 |
| 2004/0153049 A1 | 8/2004 | Hewitt et al. | |
| 2006/0074401 A1* | 4/2006 | Ross | A61M 25/0662 264/171.27 |
| 2007/0162108 A1* | 7/2007 | Carlson | A61M 25/09 623/901 |
| 2010/0035353 A1* | 2/2010 | Mourier | C07H 1/00 536/123 |
| 2015/0297292 A1* | 10/2015 | Sutermeister | A61M 37/00 606/41 |
| 2016/0256216 A1 | 9/2016 | Chang et al. | |

FOREIGN PATENT DOCUMENTS

| | | |
|---|---|---|
| CN | 104582778 | 4/2015 |
| CN | 107007922 | 8/2019 |
| EP | 1123714 | 8/2001 |
| JP | 2010-537744 A | 12/2010 |
| JP | 2015-228894 A | 12/2015 |
| WO | 2009029869 A2 | 3/2009 |
| WO | 2016040736 | 3/2016 |

OTHER PUBLICATIONS

Written Opinion for International Application No. PCT/IL2018/050882 dated Oct. 29, 2018.

* cited by examiner

MICROCATHETER

CROSS REFERENCE TO RELATED APPLICATIONS

This application is a National Phase of PCT Patent Application No. PCT/IL2018/050882 having International filing date of Aug. 8, 2018 which claims the benefit of priority of U.S. Provisional Application No. 62/542,960 filed on Aug. 9, 2017 entitled EMBOLIZATION MICROCATHETER. The contents of the above applications are all incorporated by reference as if fully set forth herein in their entirety.

TECHNICAL FIELD

The present disclosure generally relates to the field of microcatheters, and more particularly to microcatheters suitable for vascular access.

BACKGROUND

Microcatheters are increasingly used to deliver diagnostic or therapeutic agents to remote sites in a human body.

Often the target sites which one desires to access are difficult to reach and the microcatheter must be passed through narrow and tortuous blood vessels until it reaches the selected site. Accordingly, the microcatheters are required to be stiff enough at their proximal end to allow the pushing and manipulation of the microcatheter as it progresses through the body, and yet must be sufficiently flexible at the distal end to allow passage of the catheter tip through the tortuous and increasingly smaller blood vessels and at the same time not cause significant trauma to the blood vessel or to the surrounding tissue.

BRIEF SUMMARY

The present disclosure relates to microcatheters having an inner layer made of Polytetrafluoroethylene (PTFE) and a thickness of 0.0015 inch or less; a strike layer including a polyether block amide and having a thickness of 0.001 inch or less; and an outer layer, wherein different portions of the outer layer are characterized by a different durometer and wherein the distal most portion of the outer layer is made of polycarbonate-based thermoplastic polyurethane having a shore of 90A or below.

The hereindisclosed microcatheter utilizes polymers with unique properties in combination with a metallic braid having a picks per inch (PPI) ensuring that in combination with a low durometer polymer a flexible distal end is obtained and in combination with a polymer having a higher durometer a relatively stiff proximal end is provided. As a result, microcatheters with exceptional strength, resistance to kinking, and recovery from kinking, ensuring improved navigation through convoluted blood vessels are advantageously obtained. The hereindisclosed microcatheters are particularly suitable for remote site delivery, sampling and the like. The microcatheters have superior performance for remote site delivery of fluids, such as, but not limited to contrast agents and/or therapeutics. Picks per inch (PPI) is the number of weft threads per inch of woven fabric. The higher the picks per inch, the finer the material.

According to some embodiments, the distal portion of the microcatheter may have an outer layer made of a polycarbonate-based thermoplastic polyurethane providing an optimal flexibility, which enables travel through convoluted blood vessels, whereas the proximal portion of the microcatheter is made of a polyether block amide (e.g. Pebax®) providing the rigidity needed for efficiently pushing and manipulating the microcatheter.

According to some embodiments, there is provided a microcatheter comprising an inner layer, a strike layer, an outer layer and a braided skeleton located between the inner layer and the outer layer, wherein the inner layer is made of Polytetrafluoroethylene (PTFE) and has a thickness of 0.0015 inch or less, wherein the strike layer comprises a polyether block amide and has a thickness of 0.001 inch or less.

According to some embodiments, the distal portion of the outer layer is made of polycarbonate-based thermoplastic polyurethane having a shore of about 90A or below.

According to some embodiments, the polyether block amide of the strike layer may have a shore of about 55D.

According to some embodiments, the braided skeleton may be made of tungsten.

According to some embodiments, the braided skeleton may have a wire arrangement of 130 Picks Per Inch (PPI).

According to some embodiments, the distal portion of the microcatheter may have a length of about 200 mm or less.

According to some embodiments, the distal portion of the microcatheter may include two distal sections, namely a first distal section and a second distal section, wherein the first distal section is distal to the second distal section and wherein the first distal section has a lower shore than the second distal section.

According to some embodiments, the first distal section may have a shore of about 80A or below and the second distal section has a shore of about 90A or below.

According to some embodiments, the microcatheter may include an intermediary portion of its outer layer, wherein the intermediary portion includes at least a first and a second intermediary section, wherein the first intermediary section is distal to the second intermediary section and wherein the first intermediary section has a lower shore than that of the second intermediary section.

According to some embodiments, the intermediary portion may further include a third intermediary section, wherein the third intermediary section is proximal to the second intermediary section and wherein the third intermediary section has a higher shore than the second and first intermediary sections.

According to some embodiments, the first intermediary section may be made of a polyether block amide having a shore of about 40D.

According to some embodiments, the second intermediary section may be made of a polyether block amide having a shore of about 55D.

According to some embodiments, the third intermediary section may be made of a polyether block amide having a shore of about 60D.

According to some embodiments, the intermediary portion may have a length of about 400 mm or less.

According to some embodiments, a proximal portion of the outer layer may be made of a polyether block amide having a shore of about 65D of above.

According to some embodiments, the microcatheter may further include a first radiopaque marker band positioned at the first distal section of the outer layer approximately 1 mm from the microcatheter's distal end opening. According to some embodiments, the first radiopaque marker band may be made of a radiopaque alloy submerged in the first distal section's outer layer.

According to some embodiments, the microcatheter may further include a second radiopaque marker band positioned at the first distal section of the outer layer proximally to the first radiopaque marker band. According to some embodiments, the second marker band may be located positioned approximately 5-15 mm proximal to the first marker band. According to some embodiments, the second marker band may include or be a radiopaque powder embedded in the outer layer of the first distal section.

According to some embodiments, the microcatheter may further include a luer lock hub attached to the microcatheter's proximal end.

According to some embodiments, the microcatheter may further include a hydrophilic coating covering the outer layer.

According to some embodiments, the proximal portion may have a flexural rigidity of about 0.003 to 0.01 lbs-in^2.

According to some embodiments, the distal portion may have a flexural rigidity of about 0.0001 to about 0.002 lbs-in^2.

According to some embodiments, the distal portion may have a tapered inner surface.

According to some embodiments, the microcatheter may have an inner diameter of 0.50-0.7 mm and outer diameter of 0.8-0.9 mm at its distal end and 0.8-1.0 mm at its proximal end.

According to some embodiments, the microcatheter may have an active length in the range of 105 to 175 cm.

According to some embodiments, the distal section's outer layer may have an ultimate tensile strength of 9000-10000 psi and an ultimate elongation of 350-450%.

According to some embodiments, the distal section's outer layer may have an ultimate tensile strength of about 9600 psi and an ultimate elongation of approximately 400%.

According to some embodiments, there is provided a method for producing a microcatheter having an inner layer, a strike layer and an outer layer and a braided skeleton located between the inner layer and the strike layer, the method including: providing a mandrel coated with Polytetrafluoroethylene (PTFE) and a strike layer; applying a braid or coil on the mandrel; applying a polycarbonate-based thermoplastic polyurethane sleeve on the PTFE and strike layers; applying a heat shrink sleeve on the polycarbonate-based thermoplastic polyurethane sleeve; applying heat and/or pressure on the heat shrink layer thereby causing at least the outer layer to intercalate on and/or into the braid; peel off the heat shrink sleeve; and remove the mandrel.

According to some embodiments, the method may further include applying a hydrophilic coating on the microcatheter.

Certain aspects of the present disclosure may include some, all, or none of the above characteristics. One or more technical advantages may be readily apparent to those skilled in the art from the FIGURES, descriptions and claims included herein. Moreover, while specific characteristics have been enumerated above, various aspects of the present disclosure may include all, some or none of the enumerated characteristics.

Other aspects, features and advantages of the present disclosure will be further expanded upon in the drawings, detailed description and claims.

BRIEF DESCRIPTION OF THE DRAWINGS

The features and advantages of the present disclosure will become more apparent from the detailed description set forth below when taken in conjunction with the examples illustrated in the drawings in which like reference characters identify correspondingly throughout. Identical structures, elements or parts appearing in more than one FIGURE are generally labeled with the same number in all the FIGURES in which they appear. Alternatively, elements or parts appearing in more than one FIGURE may be labeled with different numbers in the different FIGURES in which they appear. The dimensions of the components and features in the FIGURES were chosen for convenience and clarity of presentation and are not necessarily shown to scale. The figures are listed below.

DETAILED DESCRIPTION

Figure 1A:
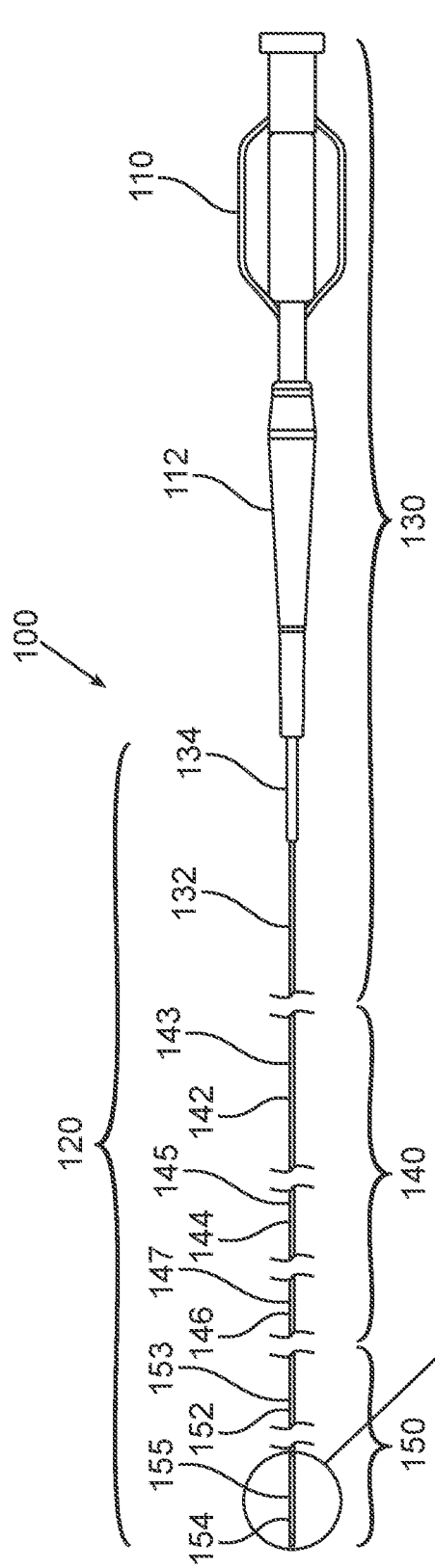
FIG. 1A schematically illustrates a microcatheter comprising an outer layer including a plurality of sections, the plurality of sections made of different polymeric materials, according to some embodiments.

The detailed description set forth below, is intended to describe various configurations, and is not intended to represent the only configurations in which the described concept may be practiced. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments of the present disclosure, there is provided a microcatheter comprising an inner layer, a strike layer, and an outer layer. A braided skeleton may be located between the inner layer and the outer layer. In one aspect, the inner layer of the microcatheter is made of Polytetrafluoroethylene (PTFE) and has a thickness of approximately 0.0015 inches or less. The strike layer may be comprised of a polyether block amide (e.g., PEBAX) and has a thickness of 0.001 inch or less. The strike layer is a connecting layer between the inner and outer layers). Because the inner layer cannot adhere to any material by heating, the strike layer may be attached to the inner layer in film cast process.

The outer layer has an overall thickness of approximately 0.082 mm to 0.095 mm. Further, the outer layer may include 2 sections: a first section and a second section. The first section of the outer layer (i.e., the distal portion) may be made of polycarbonate-based thermoplastic polyurethane having a shore of 90A or below.

As used herein the term "microcatheter" may refer to catheters having on outer diameter within the range of 0.5 mm to 1 mm. More particularly, the outer diameter of the microcatheter may be less than 2 mm, less than 1 mm, less than 0.75 mm, less than 0.60 mm, or less than 0.5 mm. According to some embodiments, the inner diameter of the microcatheter may be tapered from its proximal to its distal end by 0.3-0.75 mm, 0.4-0.7 mm or from 0.45-0.65 mm. According to some embodiments, the taper may be continuous. According to some embodiments, the microcatheter may have an outer diameter of 0.5-0.85, 0.55-0.8 or 0.6-0.75 mm at its distal end. According to some embodiments, the microcatheter may have an outer diameter of 0.75-1.5, 0.8-1.0 mm at its proximal end (i.e. the end closest to the hub). According to some embodiments, the microcatheter may have an active length in the range of 75-250 cm, 100-200 cm or 105 to 175 cm. Each possibility is a separate embodiment.

According to some embodiments, the microcatheter may be a 1.9, 2.4 French, 2.7 French or 2.8 French microcatheter. Each possibility is a separate embodiment.

As used herein the term "distal portion" may refer to the last 200 mm, 180 mm, 175 mm, 170 mm, 150 mm, 100 mm, 50 mm, or 30 mm of the microcatheter. Each possibility is a separate embodiment.

As used herein the terms "braid" and "braided skeleton" may refer to a structural element, such as a tubal element formed of a plurality of interlaced wires. According to some embodiments, the braid may be formed of at least three interlaced wires forming a tube. According to some embodiments, the braid may include 8-48 wires or 12-32 wires. As a non-limiting example, the braid may include 16 wires. Each possibility is a separate element. According to some embodiments, the wires forming the braid may have a diameter in the range of 10-60 microns such as 15-40 microns or 20-30 microns or any other suitable diameter within the range of 10-60 microns. Each possibility is a separate embodiment. As a non-limiting example, the wires forming the braid may have a diameter of 25 microns. According to some embodiments, the skeleton may extend along essentially the entire length of the catheter. According to some embodiments, the braid may be made from tungsten, stainless steel, Nickel titanium (also referred to as Nitinol), nitinol, cobalt chrome, platinum iridium, nylon or any combination thereof. Each possibility is a separate embodiment.

According to some embodiments, at least some of the wires forming the braided skeleton may be braided in a same or opposite direction, i.e. left/right handed. Advantageously, the braiding structure allows good torque-ability (better than a coiled skeleton), low flexural rigidity (i.e. good flexibility), good push-ability (better than a coiled skeleton), and superior kink-resistance.

According to some embodiments, at least some of the wires forming the braided skeleton may be non-circular/round.

According to some embodiments, the braided skeleton may have a wire arrangement of 75-250 Picks Per Inch (PPI), 100-200 PPI or 100-150 PPI. Each possibility is a separate embodiment. As a non-limiting example, the braided skeleton may have a wire arrangement of about 130 PPI. According to some embodiments, the PPI of the braid may be higher at the distal portion of the microcatheter as compared to the PPI of the intermediate and proximal portions thereof.

According to some embodiments, the different polymeric layers and/or sections may contribute to different characteristics of the layer/section and thus of the microcatheter. For example, the different polymeric layers may contribute to the elasticity, flexibility, stretch-ability, strength, hardness, rigidity, ultimate tensile strength, elongation or any other characteristic of the layer and thus the microcatheter. Each possibility is a separate embodiment.

According to some embodiments, the inner layer may have a thickness of about 0.0010 inch. According to some embodiments, the strike layer may have a thickness of about 0.0005 inch. According to some embodiments, the polyether block amide of the strike layer is a 55D shore polyether block amide. The strike layer enhances the bonding between the inner and outer layer. For example, the strike layer is connected to the inner layer during the film cast process because the inner layer comprises PTFE which cannot adhere to any material by heating.

According to some embodiments, the distal portion of the outer layer may include at least two sections, a first distal most section and a second section. The first distal most section is made of polycarbonate-based thermoplastic polyurethane (such as Pellethane™ TPU by The Lubrizol Corporation, OH, USA) and having a shore of about 80A (where shore is a measurement of hardness). The second section, adjacent the distal most section, made of polycarbonate-based thermoplastic polyurethane having a shore of about 90A. According to some embodiments, the thermoplastic polyurethane may be or include Carbothane® TPU (Lubrizol). Alternatively, both sections may be made of Carbothane® having a same or a different shore.

According to some embodiments, the distal portion may have a flexural rigidity of at least about 0.0009 [lbs-in^2]. For example, about 0.0001 to 0.002 [lbs-in^2] such as 0.0005 to 0.0.002 [lbs-in^2] or 0.0007 to 0.001 [lbs-in^2], or any in-between flexural rigidity, for example 0.0009 [lbs-in^2].

According to some embodiments, the distal portion's outer layer may have an ultimate tensile strength of 9000-10000 psi and an ultimate elongation of 350-450%. According to some embodiments, the distal portion's outer layer may have an ultimate tensile strength of about 9600 psi and an ultimate elongation of approximately 400%.

As used herein, the terms "ultimate tensile strength" and "tensile strength" may be used interchangeably and refer to the maximum stress that a material can withstand while being stretched or pulled before breaking. According to some embodiments, the microcatheter has a tensile force of at least 4N, at least 5 N, at least 7 N, or at least 10 N.

According to some embodiments, the distal portion's outer layer may have an ultimate tensile in the range of 3,000-10,000 psi, 4000-10,000; 7,500-10,000, 9,000-10,000 psi or any other range within the 2000-10000 psi range, such as but not limited to an ultimate tensile of approximately 9,600 psi. Each possibility is a separate embodiment. Additionally or alternatively, the distal portion's outer layer may have and an ultimate elongation of 350-450%, such as but not limited to an ultimate elongation approximately 400%. As used herein, the term approximately with referral to ultimate tensile and ultimate elongation may refer to +/−10%, or +/−5%, or +/−2%. Each possibility is a separate embodiment.

According to some embodiments, at least the distal portion of the microcatheter may be configured for kink-free bending. As used herein the term "kink-free bending" may refer to a bending of the distal portion, which does impede flow therethrough. According to some embodiments, the distal portion may be configured for kink-free bending at an angle of about 180 degrees. According to some embodiments, the distal portion may be configured for kink-free bending at minimum bending radius in the range of about 0.5 to 1.5 mm, for example 0.5 to 1.2, 0.5 to 1 mm, or any radius in-between.

As used herein, the term "approximately" may refer to +/−10%, or +/−5%, or +/−2%. Each possibility is a separate embodiment.

According to some embodiments, the distal portion may be 50-400 mm, 100-300 mm or 150-200 mm in length. Each possibility is a separate embodiment. According to some embodiments, the first section of the distal portion may be about 20-100 mm, or 30-75 or 40-60 mm in length. Each possibility is a separate embodiment. According to some embodiments, the second section of the distal portion may be about 75-250 mm, or 100-200 or 120-150 mm in length. Each possibility is a separate embodiment.

According to some embodiments, the distal portion may have a tapered inner surface.

According to some embodiments, the portions of the microcatheter proximal to the microcatheter's distal portion may be made from polyether block amide, such as but not limited to Pebax® (a thermoplastic elastomer (TPE) by Arkema Group, Colombes, France). It was advantageously discovered by the inventors of the present application that by having a distal portion made of polycarbonate-based thermoplastic polyurethane and the remainder of the microcatheter made of a polyether block amide, an optimal balance between flexibility and pushability of the microcatheter is achieved.

According to some embodiments, the microcatheter may include an intermediary portion, the outer layer of which including at least a first and a second intermediary section, the first intermediary section being distal to the second intermediary section. The intermediary section(s) ensure that the microcatheter gets stiffer toward its proximal end, to ensure good pushability, enable transfer of torque and provide axial rigidity. According to some embodiments, the first intermediary section may have a lower shore than that of the second intermediary section. According to some embodiments, the first intermediary section may be made of a polyether block amide having a shore of about 40D. According to some embodiments, the second intermediary section may be made of a polyether block amide having a shore of about 55D.

According to some embodiments, the outer layer of the intermediary portion may further include a third intermediary section, proximal to the second intermediary section. According to some embodiments, the third intermediary section may have a higher shore than the second and first intermediary sections. According to some embodiments, the third intermediary section may be made of a polyether block amide having a shore of about 60D.

According to some embodiments, the intermediary portion may have a length of 400 mm or less, 300 mm or less, 200 mm, or less or 150 mm or less. Each possibility is a separate embodiment.

According to some embodiments, the microcatheter may include a proximal portion. According to some embodiments, the outer layer of the proximal portion may be made of a polyether block amide having a shore of above 65D, thus providing the most rigid part of the microcatheter. According to some embodiments, the proximal portion may have a flexural rigidity (bending rigidity) of at least about 0.003. For example, about 0.003 to about 0.01 [lbs-in^2] such as 0.003-0.006 [lbs-in^2] or 0.004 to 0.005 [lbs-in^2], or any in-between flexural rigidity. According to an exemplary embodiment, the delivery/navigation section may have a flexural rigidity of about 0.0045 [lbs-in^2].

According to some embodiments, the microcatheter may include at least one radiopaque marker, e.g. 1, 2, 3, 4 or more radiopaque markers. Each possibility is a separate embodiment.

According to some embodiments, the microcatheter may include a first radiopaque marker positioned at the distal edge of the microcatheter, such as approximately 1 mm from the microcatheter's distal end opening. According to some embodiments, the first radiopaque marker may form a termination of the braid. Advantageously, positioning of the first radiopaque marker at the distal edge of the microcatheter may help preventing unraveling of the braided skeleton of the microcatheter.

As used herein, the term "distal end opening" refers to the end opening of the microcatheter leading into the lumen thereof. According to some embodiments, the distal end opening defines the termination of the microcatheter at the distal end thereof. According to some embodiments, the distal end opening may have an inner diameter essentially equal to the inner diameter of the microcatheter lumen. According to some embodiments, the distal end opening may have an inner diameter which is smaller than the inner diameter of the microcatheter lumen leading to a narrowing of the lumen toward the end thereof.

According to some embodiments, the first radiopaque marker may be made of a radiopaque alloy. According to some embodiments, the first radiopaque marker may be submerged in the polycarbonate-based thermoplastic polyurethane (TPU) layer which constructs the microcatheter's distal portion. According to some embodiments, the first radiopaque marker may overlay/cover the polycarbonate-based thermoplastic polyurethane (TPU) layer which constructs the microcatheter's distal portion. According to some embodiments, the first radiopaque marker may be made of Platinum iridium or similar radio opaque material.

According to some embodiments, the microcatheter may include a second radiopaque marker positioned proximally to the first radiopaque marker. According to some embodiments, the second marker band may be positioned approximately 5-15 mm, 7-15 mm, 10-12 mm proximal to the first marker band. According to some embodiments, the second radiopaque marker may include a radiopaque powder embedded in the outer layer of the first distal section. Without being bound by any theory, utilizing a polymeric marker at positions proximal to the microcatheter's distal edge may help maintain shaft flexibility, while providing radiopacity.

According to some embodiments, the microcatheter comprises a luer lock hub glued to or otherwise attached/connected to the proximal end of the microcatheter. According to some embodiments, the luer lock hub may have two layers of strain relief to support against kink and tight radius failures.

According to some embodiments, the microcatheter may further include a hydrophilic coating covering the outer layer. According to some embodiments, the hydrophilic coating may be configured to lower its coefficient of friction of the microcatheter within blood vessels. According to some embodiments, the coating may be configured to reduce the coefficient of friction (COF) of the microcatheter to about 0.03. According to some embodiments, the coating may be ComfortCoat® hydrophilic lubricious coatings. According to some embodiments, the coating may provide excellent lubricity, low friction and stiction, superior durability and resistance to wear, low particulate release, extended maintenance of lubricity (dry-out time), biocompatible (ISO 10993 testing), and/or hemocompatible (extended beyond ISO 10993 testing).

According to some embodiments, there is provided a method for producing the herein disclosed microcatheter comprising an inner layer, a strike layer and an outer layer and a braided skeleton located between the inner layer and the strike layer. In one aspect, the method includes providing a mandrel coated with Polytetrafluoroethylene (PTFE) and a strike layer. A braid or coil is applied on the mandrel. Additionally, a polycarbonate-based thermoplastic polyurethane sleeve is applied to the PTFE and strike layers. A heat is applied to the shrink sleeve on the polycarbonate-based thermoplastic polyurethane sleeve. Also, heat and/or pressure is applied to the heat shrink layer, thereby causing at least the outer layer to intercalate on and/or into the braid. Next the heat shrink sleeve is removed or peeled off. And then the mandrel is removed.

According to some embodiments, the method also includes applying a hydrophilic coating on the microcatheter.

According to some embodiments, the inner layer of the microcatheter may have a thickness of 0.0015 inch or less. According to some embodiments, the strike layer may have a thickness of 0.001 inch or less. According to some embodiments, the distal portion of the outer layer may be made of a polycarbonate-based thermoplastic polyurethane having a shore of 90A or below.

According to some embodiments, the microcatheter produced may have an inner diameter of 0.50-0.7 mm and outer diameter of 0.8-0.9 mm at its distal end and 0.8-1.0 mm at its proximal end. According to some embodiments, the microcatheter may have an active length in the range of 75-250 cm, 100-200 cm or 105 to 175 cm. Each possibility is a separate embodiment.

According to some embodiments, the microcatheter produced may be a 1.9, 2.4 French, 2.7 French or 2.8 French microcatheter. Each possibility is a separate embodiment.

A non-limiting example of suitable structure and proportion of a 1.9 French catheter having a continuously tapered inner diameter of 0.65 mm-0.45 mm (proximal to distal) is provided in table 1 below.

TABLE 1

| Section | Starting position [mm]-measured from catheter tip | Ending position [mm]-measured from catheter tip | Material | OD [mm] |
| --- | --- | --- | --- | --- |
| 1 | 0 | 62 | Carbothane 3585A | 0.63 |
| 2 | 62 | 190 | Carbothane 3595A | 0.7 |
| 3 | 190 | 240 | PEBAX 4033 | 0.75 |
| 4 | 240 | 280 | PEBAX 5533 | 0.8 |
| 5 | 280 | 320 | PEBAX 6333 | 0.9 |
| 6 | 320 | 1310 | PEBAX 7233 | 0.95 |

As used herein the terms "braid" and "braided skeleton" may refer to a structural element, such as a tubal element formed of a plurality of interlaced wires. According to some embodiments, the braid may be formed of at least three interlaced wires forming a tube. According to some embodiments, the braid may include 8-48 wires or 12-32 wires. As a non-limiting example, the braid may include 16 wires. Each possibility is a separate element. According to some embodiments, the wires forming the braid may have a diameter in the range of 10-60 microns such as 15-40 microns or 20-30 microns or any other suitable diameter within the range of 10-60 microns. Each possibility is a separate embodiment. As a non-limiting example, the wires forming the braid may have a diameter of 25 microns. According to some embodiments, the skeleton may extend along essentially the entire length of the catheter. According to some embodiments, the braid may be made from tungsten, stainless steel, Nickel titanium (also referred to as Nitinol), nitinol, cobalt chrome, platinum iridium, nylon or any combination thereof. Each possibility is a separate embodiment.

According to some embodiments, at least some of the wires forming the braided skeleton may be braided in a same or opposite direction.

According to some embodiments, at least some of the wires forming the braided skeleton may be non-circular/round.

According to some embodiments, the braided skeleton may have a wire arrangement of 75-250 Picks Per Inch (PPI), 100-200 PPI or 100-150 PPI. Each possibility is a separate embodiment. As a non-limiting example, the braided skeleton may have a wire arrangement of about 130 PPI. According to some embodiments, the PPI of the braid may be higher at the distal portion of the microcatheter as compared to the PPI of the intermediate and proximal portions thereof.

According to some embodiments, the different polymeric layers and/or sections may contribute to different characteristics of the layer/section and thus of the microcatheter. For example, the different polymeric layers may contribute to the elasticity, flexibility, stretch-ability, strength, hardness, rigidity, ultimate tensile strength, elongation or any other characteristic of the layer and thus the microcatheter. Each possibility is a separate embodiment.

According to some embodiments, the inner layer may have a thickness of about 0.0010 inch, as essentially described herein. According to some embodiments, the strike layer may have a thickness of about 0.0005 inch, as essentially described herein. According to some embodiments, the polyether block amide of the strike layer is a 55D shore polyether block amide, as essentially described herein.

According to some embodiments, the distal portion of the outer layer may include at least two sections, a first distal most section made of polycarbonate-based thermoplastic polyurethane having a shore of about 80A; and a second section, adjacent the distal most section, made of polycarbonate-based thermoplastic polyurethane having a shore of about 90A, as essentially described herein. According to some embodiments, the thermoplastic polyurethane may be or include Carbothane® TPU (Lubrizol).

According to some embodiments, the distal portion may have a flexural rigidity of at least about lbs-in^2, as essentially described herein.

According to some embodiments, the distal portion's outer layer may have an ultimate tensile strength of 9000-10000 psi and an ultimate elongation of 350-450%, as essentially described herein. According to some embodiments, the distal portion's outer layer may have an ultimate tensile strength of about 9600 psi and an ultimate elongation of approximately 400%, as essentially described herein.

According to some embodiments, the distal portion's outer layer may have an ultimate tensile in the range of 3,000-10,000 psi, 4000-10,000; 7,500-10,000, 9,000-10,000 psi or any other range within the 2000-10000 psi range, such as but not limited to an ultimate tensile of approximately 9,600 psi. Each possibility is a separate embodiment. Additionally or alternatively, the distal portion's outer layer may have and an ultimate elongation of 350-450%, such as but not limited to an ultimate elongation approximately 400%. As used herein, the term approximately with referral to ultimate tensile and ultimate elongation may refer to +/−10%, or +/−5%, or +/−2%. Each possibility is a separate embodiment.

According to some embodiments, the distal portion may be 50-400 mm, 100-300 mm or 150-200 mm in length, as essentially described herein. Each possibility is a separate embodiment. According to some embodiments, the first section of the distal portion may be about 20-100 mm, or 30-75 or 40-60 mm in length, as essentially described herein. Each possibility is a separate embodiment. According to some embodiments, the second section of the distal portion may be about 75-250 mm, or 100-200 or 120-150 mm in length, as essentially described herein. Each possibility is a separate embodiment.

Reference is now made to FIG. 1A which schematically illustrates a microcatheter 100 having an outer layer including a plurality of sections, the plurality of sections made of different polymeric materials, according to some embodiments. The proximal end 130 of microcatheter 100 includes a hub 110 which is molded on or otherwise attached to catheter shaft 120 of microcatheter 100. According to some embodiments, proximal end 130 may have a length of 100-200 cm.

Hub 110 is configured to allow access to the lumen of catheter shaft 120 for a variety of functions, such as the injection of fluids or drugs, or the introduction of guidewires. Hub 110 includes a strain relief 112, preferably mechanically coupled to hub 110. Strain relief 112 may be made of a polymeric material and may as illustrated, be tapered at its distal end and be configured to provide structural support to catheter shaft 120, thereby help avoiding kinking of catheter shaft 120. The proximal end 130 of catheter shaft 120, attached to strain relief 112, includes an outer layer 132 made of a polyether block amide having a shore of about 70D and/or a flexural modulus of about 74,000 psi, such as, but not limited to Pebax® 7233. According to some embodiments, proximal end 132 may have a length of 800-1200 mm (e.g. about 1000 mm). Optionally, part of outer layer 132 may include a heat shrink material 134 covering the joint between strain relief 112 and catheter shaft 120.

Adjacent proximal end 130, at the intermediary part 140 of catheter shaft 120, is another section 142 having an outer layer 143 made of a polyether block amide having a shore of about 60D and/or a flexural modulus of about 41,000 psi, such as but not limited to Pebax® 6333 followed by section 144 having an outer layer 145 made of a polyether block amide having a shore of about 55D and/or a flexural modulus of about 25,000 psi, such as but not limited to Pebax® 5533 and section 146 having an outer layer 147 made of a polyether block amide having a shore of about 40D and/or a flexural modulus of about 11,000 psi, such as but not limited to Pebax® 4033. According to some embodiments, section 142 may have a length of 20-60 mm (e.g. about 40 mm). According to some embodiments, section 144 may have a length of 20-60 mm (e.g. about 40 mm). According to some embodiments, intermediary part 140 may have a length of 100-120 mm. According to some embodiments, section 146 may have a length of 30-70 mm (e.g. about 50 mm).

Figure 1B:
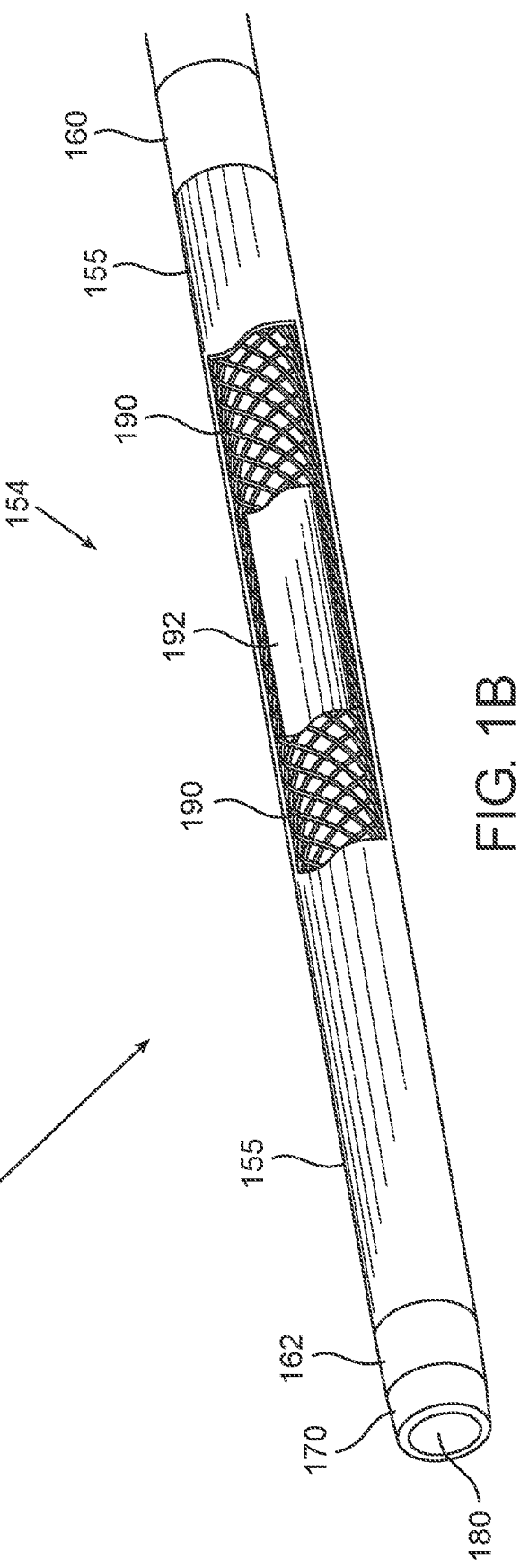
FIG. 1B schematically illustrates a perspective, cutaway view of the distal end of the microcatheter of FIG. 1A illustrating the outer layer, the strike layer, the inner layer, the braided skeleton located between the inner layer and the outer layer.

Distal end 150 of catheter shaft 120 includes section 152 having an outer layer 153 made of polycarbonate-based thermoplastic polyurethane having a shore of about 80A and/or a flexural modulus of about 1500 psi, such as but not limited to Carbothane PC-3585-A, a proximal marker 160 (seen in FIG. 1B), section 154 having an outer layer 155 made of polycarbonate-based thermoplastic polyurethane having a shore of about 90A and/or a flexural modulus of about 6400, such as but not limited to Carbothane PC-3595-A and a distal marker 162 (also seen in FIG. 1B). According to some embodiments, distal end 150 may have a length of 175-200 mm. According to some embodiments, section 152 may have a length of 100-200 mm (e.g. about 150 mm). According to some embodiments, section 154 may have a length of 40-80 mm (e.g. about 60 mm). According to some embodiments, proximal marker 160 may be a radiopaque powder embedded in the outer layers 153 or 155, as essentially described herein. According to some embodiments, proximal marker 160 may be positioned approximately 1 mm from the distal end opening 180. According to some embodiments, distal marker 162 may be a radiopaque alloy submerged in outer layer 155. According to some embodiments, distal marker 162 may be positioned 5-15 mm proximally from distal end opening 180. According to some embodiments, outer layers 132, 143, 145, 147, 153 and/or 155 may have an overall thickness of approximately 0.082 mm to 0.095 mm.

Reference is now made to FIG. 1B which schematically illustrates a perspective, cutaway view of the distal part of distal end 150 of microcatheter 100 shown in FIG. 1A extending from proximal marker 160 to tip 170 and encompassing section 154 of catheter shaft 120. As stated above, section 154 includes an outer layer 155 made of polycarbonate-based thermoplastic polyurethane having a shore of about 90A and/or a flexural modulus of about 6400. As seen from the exploded view, underneath outer layer 155 is a braid 190. According to some embodiments, braid 190 extends along the entire length of shaft 120. Alternatively, braid 190 extends along only a portion of shaft 120, such as only along section 154, along sections 152 and 154, along sections 152, 154 and 146, along sections 152, 154, 146 and 144, along sections 152, 154, 146, 144 and 142, or along sections 152, 154, 146, 144, 142 and 142. Each possibility is a separate embodiment. Preferably, braid 190 has a picks-per-inch (PPI) ensuring, that in combination with a low durometer polymer, a flexible distal end is obtained, and in combination with a polymer having a higher durometer a relatively stiff proximal end is provided (e.g. 130 PPI). Underneath braid 190 is an inner layer 192 (also referred to as a "liner" or "inner liner"), which may be made of Polytetrafluoroethylene (PTFE). According to some embodiments, inner layer 192 may have a thickness of 0.0015 inch or less.

EXAMPLES

Example 1—Microcatheter Flexibility

The purpose of the study was to characterize the flexibility of the hereindisclosed microcatheter comparatively to a leading commercially available microcatheter. The study was performed on a 2.8 Fr-150 cm as disclosed herein (also referred to as Drakon™) manufactured at Nordson Medical (Sunnyvale, previously Vention Medical) by the complete manufacturing process including receiving inspection, product manufacturing, hydrophilic coating, QA inspection, packaging and sterilization.

The flexibility of the catheter distal region is of interest as its characteristics define the navigation abilities of the catheter. Specifically, the distal 20-30 mm of the catheter is most likely the region to reach the most distal, tortuous anatomy. The distal region (the distal 24 mm) of the catheter was fixed perpendicular to an analytical scale. The distal tip was then placed on a displacement jig which caused a 5.25 mm displacement. The displacement force (flexibility) was then measured using the analytical scale.

The results obtained for 5 of herein disclosed 2.8 French microcatheters (Drakon™) as well as that of 5 2.8 French of another commercially available microcatheter (control) as summarized in Table 2 below (p-value 0.0007).

TABLE 2

| Sample | Measured Value 1 (grams) | Measured Value 2 (grams) | Measured Value 3 (grams) | Average (grams) | Standard Deviation (grams) |
|---|---|---|---|---|---|
| Drakon (2.8 Fr. - 150 cm) | | | | | |
| 1 | 0.2 | 0.199 | 0.208 | 0.202 | 0.005 |
| 2 | 0.143 | 0.145 | 0.16 | 0.150 | 0.009 |
| 3 | 0.185 | 0.19 | 0.18 | 0.185 | 0.005 |
| 4 | 0.215 | 0.223 | 0.24 | 0.226 | 0.012 |
| 5 | 0.23 | 0.22 | 0.212 | 0.220 | 0.009 |
| Average and Standard Deviation of all tested sample and measurement: | | | | 0.197 | 0.030 |
| Control (2.8 Fr. - 130 cm) | | | | | |
| 1 | 0.305 | 0.305 | 0.295 | 0.302 | 0.006 |
| 2 | 0.318 | 0.317 | 0.316 | 0.317 | 0.001 |
| 3 | 0.285 | 0.276 | 0.277 | 0.279 | 0.005 |
| 4 | 0.295 | 0.299 | 0.308 | 0.300 | 0.007 |
| 5 | 0.29 | 0.281 | 0.27 | 0.280 | 0.010 |
| Average and Standard Deviation of all tested sample and measurement: | | | | 0.296 | 0.016 |

As seen from the table, the hereindisclosed microcatheter (Drakon™) demonstrated a significantly superior flexibility than that of the commercially available microcatheter (control), namely by 66% percent.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. According to some embodiments, the term "comprising" may be replaced by the term "consisting essentially of" or "consisting of".

The term "about" refers to a reasonable variation from a stated amount that retains the ability to achieve one or more functional effect to substantially the same extent as the stated amount. The term may also refer herein to a value of plus or minus 10% of the stated value; or plus or minus 5%, or plus or minus 1%, or plus or minus 0.5%, or plus or minus 0.1%, or any percentage in between.

While a number of exemplifying aspects and embodiments have been discussed above, those of skill in the art will envisage certain modifications, additions and subcombinations thereof. It is therefore intended that the following appended claims and claims hereafter introduced be interpreted to include all such modifications, additions and sub-combinations as are within their true spirit and scope.

The invention claimed is:

1. A method for producing a microcatheter comprising an inner layer, a strike layer and an outer layer and a braided skeleton located between the inner layer and the strike layer, the method comprising:
providing a mandrel coated with Polytetrafluoroethylene (PTFE), thereby forming an inner layer, and a strike layer; applying a braided skeleton or coil on the mandrel;
applying a polycarbonate-based thermoplastic polyurethane sleeve on the PTFE and strike layers, thereby forming an outer layer;
applying a heat shrink sleeve on the polycarbonate-based thermoplastic polyurethane sleeve;
applying heat and/or pressure on the heat shrink layer sleeve, thereby causing at least the outer layer to intercalate on and/or into the braid;
peeling off the heat shrink sleeve;
removing the mandrel.

2. The method of claim 1, wherein the inner layer has a thickness of 0.0015 inch or less, wherein the strike layer comprises a polyether block amide and has a thickness of 0.001 inch or less, and wherein at least a portion of the polycarbonate-based thermoplastic polyurethane sleeve has a shore of 90A or below.

3. The method of claim 2, wherein the polyether block amide of the strike layer has a shore of about 55D.

4. The method of claim 1, wherein the braided skeleton has a wire arrangement of 130 Picks Per Inch (PPI).

5. The method of claim 1, wherein the polycarbonate-based thermoplastic polyurethane sleeve comprises a distal portion comprising a first distal section and a second distal section, wherein the first distal section is distal to the second distal section and wherein the first distal section has a lower shore than the second distal section.

6. The method of claim 5, wherein the first distal section has a shore of 80A or below and the second distal section has a shore of 90A or below.

7. The method of claim 5, wherein the polycarbonate-based thermoplastic polyurethane sleeve comprises an intermediary portion comprising at least a first intermediary section and a second intermediary section, wherein the first intermediary section is distal to the second intermediary section and wherein said first intermediary section has a lower shore than that of the second intermediary section.

8. The method of claim 7, wherein the intermediary portion further comprises a third intermediary section, wherein the third intermediary section is proximal to the second intermediary section and wherein the third intermediary section has a higher shore than the second and first intermediary sections.

9. The method of claim 8, wherein the first intermediary section is made of a polyether block amide having a shore of about 40D.

10. The method of claim 9, wherein the second intermediary section is made of a polyether block amide having a shore of about 55D.

11. The method of claim 10, wherein the third intermediary section is made of a polyether block amide having a shore of about 60D.

12. The method of claim 8, wherein the intermediary portion has a length of 400 mm or below.

13. The method of claim 5, wherein the outer layer further comprises a proximal portion, wherein the proximal portion of the outer layer is made of a polyether block amide having a shore of above 65D.

14. The method of claim 1, wherein the microcatheter has an inner diameter of 0.50-0.7 mm and outer diameter of 0.8-0.9 mm at its distal end and 0.8-1.0 mm at its proximal end, and an active length in the range of 105 to 175 cm.

* * * * *